US008901361B2

(12) United States Patent
Pasquinet et al.

(10) Patent No.: US 8,901,361 B2

(45) Date of Patent: Dec. 2, 2014

(54) METHOD FOR SYNTHESIZING 3,5-DICHLOROANISOLE FROM 1,3,5-TRICHLOROBENZENE

(75) Inventors: Eric Pasquinet, Saint Avertin (FR); Anne Wuillaume, Tours (FR); Didier Poullain, St. Avertin (FR); Etienne Kosciusko-Morizet, Sevres (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/522,291

(22) PCT Filed: Jan. 12, 2011

(86) PCT No.: PCT/EP2011/050288

§ 371 (c)(1), (2), (4) Date: Jan. 7, 2013

(87) PCT Pub. No.: WO2011/086071

PCT Pub. Date: Jul. 21, 2011

(65) Prior Publication Data

US 2013/0178655 A1 Jul. 11, 2013

(30) Foreign Application Priority Data

Jan. 14, 2010 (FR) ...................................... 10 50232

(51) Int. Cl.

| | |
|---|---|
| ***C07C 17/00*** | (2006.01) |
| ***C07C 22/00*** | (2006.01) |
| ***C07C 25/00*** | (2006.01) |
| ***C07C 41/01*** | (2006.01) |
| ***C07C 209/10*** | (2006.01) |
| ***C07C 209/18*** | (2006.01) |
| ***C07C 41/16*** | (2006.01) |
| ***C07C 201/10*** | (2006.01) |

(52) U.S. Cl.

CPC ............... *C07C 41/01* (2013.01); *C07C 209/10* (2013.01); *C07C 209/18* (2013.01); *C07C 41/16* (2013.01); *C07C 201/10* (2013.01)

USPC ......................................................... 570/190

(58) Field of Classification Search

CPC ....................................................... C07C 41/01

See application file for complete search history.

(56) References Cited

U.S. PATENT DOCUMENTS 2,615,928 A * 10/1952 Jolly ............................ 585/710
4,952,733 A 8/1990 Ott et al.

FOREIGN PATENT DOCUMENTS

JP S5331631 3/1978

OTHER PUBLICATIONS

Anderson, Neal, Practical Process Research and Development, 2000, pp. 81 to 85.*
Preliminary Search Report issued on Sep. 13, 2010 for French Application No. FR 1050232.
Testaferri, et al., "The reactions of unactivated aryl halides with sodium methoxide in HMPA", Tetrahedron, Elsevier Science Publishers, Amsterdam, NL LNKD-DOI: 10.1016/S0040-4020(01)97647-1, vol. 39, No. 1, Jan. 1, 1983, pp. 193-197, XP002168754.
Database CA [Online] Chemical Abstracts service, Columbus, Ohio, US; 1978, Kondo, Fumihiko, et al, "Alkoxy aromatic compounds", XP002597364, retrieved from STN Database accession No. 1978: 508636 and JP 53 031631 A (Kawaken Fine Chemicals Co., Ltd., Japan), Mar. 25, 1978.
International Search Report issued on Jun. 22, 2011 for International Application No. PCT/EP2011/050288.

* cited by examiner

*Primary Examiner* — Clinton Brooks

(74) *Attorney, Agent, or Firm* — Knobbe, Martens, Olson & Bear, LLP

(57) ABSTRACT

A method for synthesizing 3,5-dichloroanisole from 1,3,5-trichloro-benzene is proved. The method may comprises: a) the reaction between 1,3,5-trichloro-benzene and a methanolate of an alkaline or alkaline-earth metal in a first solvent chosen from among dimethylsulfoxide and 1,1,3,3-tétramethylurea, b) the precipitation of the product resulting from step a) in a second solvent which is not included among substances considered carcinogenic, mutagenic and/or toxic for reproduction by Regulation (EC) no 1272/2008 of the European Parliament and of the Council of 16 Dec. 2008, then c) the recovery of the precipitate thus obtained. The method may be applied to synthesize 1,3,5-triamino-2,4,6-trinitrobenzene in which 3,5-dichloroanisole is an intermediate product.

15 Claims, No Drawings

METHOD FOR SYNTHESIZING 3,5-DICHLOROANISOLE FROM 1,3,5-TRICHLOROBENZENE

RELATED APPLICATIONS

This application is a U.S. National Phase of International Application No. PCT/EP2011/050288, filed Jan. 12, 2011, designating the U.S., and published in French as WO 2011/086071 on Jul. 21, 2011 which claims the benefit of French Patent Application No. 10 50232 filed Jan. 14, 2010.

TECHNICAL FIELD

The present invention relates to a method allowing the synthesis of 3,5-dichloroanisole from 1,3,5-trichlorobenzene and which has the advantages, among others, of having a high yield and of not requiring any additional purification operation of the 3,5-dichloroanisole produced during this synthesis, which means that it is of strong interest from an economic viewpoint.

This method can find application in the synthesis of 1,3,5-triamino-2,4,6-trinitrobenzene of which 3,5-dichloroanisole is an intermediate product.

BACKGROUND 1,3,5-triamino-2,4,6-trinitrobenzene is a powerful explosive of particularly high insensitivity to shocks, vibrations, impacts and fire making it an explosive of choice for the weapons industry.

This explosive is obtained in particular by nitration of 3,5-dichloroanisole followed by amination of the resulting trinitrated compound. One method allowing these reactions of nitration and amination to be carried out is described in U.S. Pat. No. 4,952,733 (hereinafter reference [1]).

3,5-dichloroanisole is commercially available but is relatively costly to purchase, hence the advantage for explosive manufacturers to be able themselves to conduct the synthesis thereof.

The literature regarding the synthesis of 3,5-dichloroanisole is extremely sparse and in practice is limited to an article published in 1983 by L. Testaferri et al. in *Tetrahedron,* 39(1), 193-197 (hereinafter reference [2]) and to the Japanese patent application published under number 53-31631 (hereinafter reference [3]).

Reference [2] teaches that it is possible to obtain mono-, di- and trichloroanisoles by nucleophilic substitution of the corresponding di-, tri- and tetra-chlorobenzenes by methanolate ions on the express condition that this substitution reaction is conducted in hexamethylphosphoramide (HMPA), also known as <<hexamethylphosphoric triamide>>.

Therefore, in this reference, 3,5-dichloroanisole is synthesized by adding sodium methanolate to a suspension, previously held under nitrogen at 120° C., of 1,3,5-trichlorobenzene in HMPA and leaving to react for one hour. It is then isolated by extraction with ether and purified by chromatography on a silica gel column using a mixture of petroleum ether and ethyl ether as eluent.

The yield of this synthesis is 78%.

It happens that HMPA is classified under the regulations of the European Union among CMR substances i.e. substances which are considered as potentially or proven to be carcinogenic, mutagenic and/or toxic for reproduction, making the use of this solvent prohibitive in a synthesis method intended to be implemented on industrial scale.

Also, the fact that the 3,5-dichloroanisole must be purified on completion of the synthesis by column chromatography in particular, means that the production of this compound is made cumbersome by increasing the number of operations to be conducted as well as the volume of consumed organic solvents, and is economically penalizing for production on an industrial scale.

Reference [3] proposes synthesizing alkoxy aromatic compounds such as 3,5-dichloroanisole, by causing the corresponding haloaromatic compounds to react with an alkoxide of an alkaline metal in the presence of N,N'-dimethylimidazolidinone.

Therefore, in this reference, 3,5-dichloroanisole is synthesized by causing 1,3,5-trichlorobenzene to react with sodium methanolate in N,N'-dimethylimidazolidinone, for 18 hours at a temperature of 100±5° C. The 3,5-dichloroanisole is then extracted from the reaction medium using ether.

N,N'-dimethylimidazolidinone, compared with HMPA, has the advantage of not being classified among CMR substances by the European Union regulation.

On the other hand, reference [3] shows that the yield of the synthesis of 3,5-dichloroanisole in this solvent is largely insufficient since it is only 47.2%.

The Inventors have set themselves the objective of providing a method which, while not using any solvent considered to have potential or proven harmful effects on the health of man or animals, allows the synthesis of 3,5-dichloroanisole at the lowest possible cost.

From this perspective, the Inventors have more particularly set themselves the goal that this synthesis method should have a high yield, should lead to obtaining sufficiently pure 3,5-dichloroanisole so that it is not necessary for it to undergo any additional purification operation after this synthesis, and should only have recourse to operations that are simple to implement.

DESCRIPTION OF CERTAIN INVENTIVE ASPECTS

These objectives are achieved by the present invention which proposes a method allowing the synthesis of 3,5-dichloroanisole from 1,3,5-trichlorobenzene, which comprises:

a) the reaction between 1,3,5-trichlorobenzene and a methanolate of an alkaline or alkaline-earth metal in a first solvent chosen from among dimethylsulfoxide, 1,1,3,3-tetramethylurea and mixtures thereof;

b) the precipitation of the product resulting from step a) in a second solvent which is not included among the substances considered to be carcinogenic, mutagenic and/or toxic for reproduction by Regulation (EC) no 1272/2008 of the European Parliament and of the Council of 16 Dec. 2008; followed by c) the recovery of the precipitate thus obtained.

Therefore, according to the invention, first 1,3,5-trichlorobenzene is caused to react with a methanolate of an alkaline or alkaline-earth metal in dimethylsulfoxide and/or in 1,1,3,3-tetramethylurea, these two solvents having the advantage of not being classified among CMR substances by the European regulation.

The 3,5-dichloroanisole thus produced is then separated from the reaction medium by causing it to precipitate in a second solvent which is not classified either among CMR substances by the European Union regulation.

The precipitate formed is then collected.

In this way, as illustrated in the examples below, 3,5-dichloroanisole is obtained with a yield which is close to 90% and in some cases much higher than this value.

According to the invention, the first solvent is preferably dimethylsulfoxide for the simple reason that its cost is currently lower than that of 1,1,3,3-tetramethylurea.

According to the invention, the methanolate may be a methanolate of an alkaline metal, e.g. of sodium, potassium or lithium, or a methanolate of alkaline-earth metal, e.g. magnesium, calcium or barium.

However, preference is given to sodium methanolate.

This methanolate can be used in solid form or in the form of an alcohol solution, e.g. methanol. In all cases, it is preferably used to the proportion of 1 to 3 molar equivalents, better still 1 to 2 molar equivalents, and most preferably 1 to 1.3 molar equivalent relative to 1,3,5-trichlorobenzene.

The reaction between the methanolate and 1,3,5-trichlorobenzene is conducted at a temperature possibly ranging from 20° C. up to the boiling point of the first solvent, but which is advantageously 40 to 120° C. and more preferably 60 to 100° C.

The reaction time may range from 15 minutes to 24 hours depending on the kinetics thereof at the temperature used, but it is preferably from 15 minutes to 5 hours.

Also, the reaction can be conducted by simultaneously adding the methanolate, 1,3,5-trichlorobenzene and the first solvent to one same reactor by subjecting them to the above-mentioned conditions.

However it may be advantageous, in order to control the exothermal nature of the reaction, to add either the methanolate portion-wise to a mixture of 1,3,5-trichlorobenzene and solvent already present in the reactor, or the 1,3,5-trichlorobenzene portion-wise to a mixture of methanolate and solvent already present in the reactor.

According to the invention, the second solvent may be any solvent in which 3,5-dichloroanisole is scarcely soluble, even insoluble. However, for reasons of simplicity and cost it is preferred that water is used, and better still water whose temperature does not exceed 20° C.

The method of the invention may additionally, after the recovery of the precipitate, comprise an operation to wash this precipitate if it is desired to increase the purity of the 3,5-dichloroanisole, which typically will be the case if the degree of purity of this compound in this recovered precipitate is less than 90%.

In this case, the washing operation is advantageously performed with a third solvent which also is chosen from among the solvents which are not classified under CMR substances by the European Union regulation.

Here also, this third solvent may be any solvent in which 3,5-dichloroanisole is scarcely soluble, even insoluble, but for reasons of simplicity and cost it is preferably water and better still water whose temperature does not exceed 20° C.

In this manner, as illustrated in the examples below, 3,5-dichloroanisole is obtained whose degree of purity is always at least 90% and is typically of the order of 96-98%.

The method of the invention, after the recovery of the precipitate or optionally after the washing thereof, may further comprise an operation of drying this precipitate if the presence of a small quantity of solvent, water in particular, in said precipitate proves to be a hindrance for the subsequent use of the 3,5-dichloroanisole.

This drying operation is conducted for example by drying under a flow of air at ambient temperature or higher, by lyophilisation, by using a supercritical fluid ($CO_2$ for example) or by vacuum drying at ambient temperature or a temperature higher than ambient temperature.

Having regard to its degree of purity, the 3,5-dichloroanisole obtained with the method of the invention can be used to synthesize 1,3,5-triamino-2,4,6-trinitrobenzene without the need for any prior purification operation thereof.

A further subject of the invention is therefore a method for synthesizing 1,3,5-triamino-2,4,6-trinitro-benzene, which comprises:

i) the synthesis of 3,5-dichloroanisole using a method such as previously defined; then ii) the conversion of the 3,5-dichloroanisole to 1,3,5-triamino-2,4,6-trinitrobenzene.

This conversion can be performed in particular by nitration of the 3,5-dichloroanisole followed by amination of the compound resulting from this nitration, as described in reference [1].

Other characteristics and advantages of the invention will become better apparent on reading the following examples which are evidently given as a non-limiting illustration.

DETAILED DESCRIPTION OF CERTAIN ILLUSTRATIVE EMBODIMENTS

Example 1

A 50 mL three-necked flask is charged with 5 g (27.6 mmoles) of 1,3,5-trichlorobenzene that is placed in suspension in 20 mL of dimethylsulfoxide. To this suspension is added 1.78 g (33.0 moles) of sodium methanolate. The mixture thus obtained is heated to 62° C., under agitation, for 5 hours 30.

After this time, the content of the flask is lowered to ambient temperature and it is poured into 200 mL of iced water. A white solid is precipitated.

This solid is recovered by filtering, washed three times with 20 mL of iced water, then vacuum dried at ambient temperature.

This gives 4.31 g of a white powder whose analysis by nuclear magnetic resonance (NMR), conforming to that of the expected 3,5-dichloro-anisole, is as follows:

$^{1}$H NMR ($CDCl_3$, 200 MHz) δ (ppm): 3.75 (s, 3H); 6.77 (d, J=2 Hz, 2H); 6.93 (t, J=2 Hz, 1H);

$^{13}$C NMR ($CDCl_3$, 50 MHz) δ (ppm): 55.4; 112.9; 120.7; 135.2; 160.4.

Also, analysis by gas phase chromatography coupled with mass spectrometry (GC-MS), shows that the 3,5-dichloroanisole thus obtained has a degree of purity of 98%.

The conditions for performing GC-MS analysis are the following:

column: CP-Sil 8 vector gas: helium, 1.0 mL/min injector temperature: 250° C.

injected volume: 1 μL oven temperature: 1 min at 50° C., then 20° C./min up to 100° C., then 40° C./min up to 240° C., then 1 min at 240° C.

The yield is 88%.

Example 2

A 50 mL three-necked flask is charged with 5 g (27.6 mmoles) of 1,3,5-trichlorobenzene and 1.79 g (33.1 mmoles) of sodium methanolate that are placed in suspension in 10 mL of 1,1,3,3-tetramethylurea. This suspension is heated to 62° C., under agitation, for 1 hour, then to 100° C. for 20 hours 30. After this time 1.49 g (27.6 mmoles) of sodium methanolate is added and heating at 100° C. is continued, still under agitation, for 3 hours 30.

After this time, the content of the flask is lowered to ambient temperature and poured into 100 mL of iced water. A white solid is precipitated. This solid is recovered by filtering, washed three times with 20 mL of iced water, then vacuum dried at ambient temperature.

This gives 4.24 g de 3,5-dichloroanisole in the form of a white powder whose analysis by GC-MS (under the same conditions as previously) shows that it has a degree of purity of 97%.

The yield is 87%.

Example 3

A 50 mL three-necked flask is charged with 5 g (27.6 mmoles) of 1,3,5-trichlorobenzene that is placed in suspension in 20 mL of dimethylsulfoxide. To this suspension are added 5.97 g of a 30% solution of sodium methanolate in methanol, i.e. 33.1 mmoles of sodium methanolate. The mixture thus obtained is heated to 80° C. under agitation for 3 hours.

After this time, the content of the flask is treated as described in Example 1 above.

This gives 4.34 g of 3,5-dichloroanisole in the form of a white powder whose analysis by GC-MS (under the same conditions as previously) shows that it has a degree of purity of 97%.

The yield is 89%.

Example 4

A 50 mL three-necked flask is charged with 1.79 g (33.1 mmoles) of sodium methanolate that is placed in suspension in 10 mL of dimethylsulfoxide. This suspension is heated to 60° C. then 5 g (27.6 mmoles) of previously melted 1,3,5-trichlorobenzene are added portion-wise. Heating at 62° C. is continued still under agitation for 3 hours.

After this time, the content of the flask is treated as described in Example 2 above.

This gives 4.24 g of 3,5-dichloroanisole in the form of a white powder whose analysis by GC-MS (under the same conditions as previously) shows that it has a degree of purity of 97%.

The yield is 87%.

Example 5

A 1 L three-necked flask is charged with 100 g (551 mmoles) of 1,3,5-trichlorobenzene that is placed in suspension in 400 mL of dimethylsulfoxide. This suspension is heated to 80° C., under agitation, then 119.06 g of a 30% solution of sodium methanolate are added drop-wise, i.e. 661.2 mmoles of sodium methanolate. Heating is continued up to 90° C., still under agitation, for 3 hours 10.

After this time, the content of the flask is lowered too ambient temperature and it is poured into 4 L of iced water. A white solid is precipitated. This solid is recovered by filtering, washed three times with 250 mL of iced water, then vacuum died at ambient temperature.

This gives 95.55 g of 3,5-dichloroanisole in the form of a white powder whose analysis by GC-MS (under the same conditions as previously) shows that it has a degree of purity of 96%.

The yield is 98%.

Example 6

A 2 L reactor is charged with 107.18 g (1.984 mole) of sodium methanolate that is placed in suspension in 600 mL of dimethylsulfoxide. This suspension is heated, under agitation, to 60° C. Then 300 g (1.653 mole) of solid 1,3,5-trichlorobenzene are added portion-wise. Heating is continued at 62° C., still under agitation, for 2 hours 50.

After this time, the content of the flask is lowered to ambient temperature and it is poured into 6 L of iced water. A white solid is precipitated. This solid is recovered by filtering, washed three times with 600 mL of iced water, then vacuum dried at ambient temperature.

This gives 282.17 g of 3,5-dichloroanisole in the form of a white power for which GC-MS analysis (under the same conditions as previously) shows that it has a degree of purity of 92%.

The yield is 96%.

Example 7

A 100 mL thee-necked flask is charged with 2.31 g (33 mmoles) of potassium methanolate and 33 mL of dimethylsulfoxide. This suspension is heated to 60° C., under agitation, then 5 g (27.6 mmoles) of 1,3,5-trichlorobenzene are added portion-wise. Heating is continued at 62° C., still under agitation, for 5 hours after which 1 g of potassium methanolate is added to the reaction medium, then heating is continued for 2 additional hours.

After this time, the content of the flask is lowered to ambient temperature and it is poured into 330 mL of iced water. A white solid is precipitated. This solid is recovered by filtering, washed four times with 50 mL of iced water, then vacuum dried at ambient temperature.

This gives 4.25 g of 3,5-dichloroanisole in the form of a white powder whose NMR analysis shows that it has a degree of purity of 90%.

The yield is 87%.

CITED REFERENCES

[1] U.S. Pat. No. 4,952,733
[2] L. Testaferri et al., *Tetrahedron* (1983), 39(1), 193-197
[3] Japanese patent application published under number 53-31631

What is claimed is:

1. A method for synthesizing 3,5-dichloro-anisole from 1,3,5-trichlorobenzene, which comprises:

a) reacting 1,3,5-trichloro-benzene with a methanolate of an alkaline or alkaline-earth metal in a first solvent selected from the group consisting of dimethylsulfoxide, 1,1,3,3-tetramethylurea and mixtures thereof;

b) precipitating the product resulting from a) in a second solvent which is water; then c) recovering the precipitate obtained in b).

2. The method according to claim 1, wherein the first solvent is dimethylsulfoxide.

3. The method according to claim 1, wherein the methanolate is selected from the group consisting of the methanolates of sodium, potassium, lithium, magnesium, calcium and barium.

4. The method according to claim 3, wherein the methanolate is sodium methanolate.

5. The method according to claim 1, wherein the methanolate is used to the proportion of 1 to 3 molar equivalents relative to the 1,3,5-trichlorobenzene.

6. The method according to claim 1, wherein a) is conducted at a temperature of 40 to 120° C.

7. The method according to claim 1, wherein a) is conducted for a time ranging from 15 minutes to 24 hours.

8. The method according to claim 1, which further comprises washing the precipitate recovered at c) with a third solvent which is water.

9. The method according to claim 8, wherein the third solvent is water whose temperature does not exceed 20° C.

10. The method according to claim 1, which further comprises drying the precipitate recovered at c).

11. A method for synthesizing 1,3,5-triamino-2,4,6-trinitrobenzene, which comprises:

i) synthesizing 3,5-dichloroanisole using a method as defined in claim 1; then ii) converting the 3,5-dichloroanisole to 1,3,5-triamino-2,4,6-trinitro-benzene.

12. The method according to claim 1, wherein the methanolate is used to the proportion of 1 to 2 molar equivalents relative to the 1,3,5-trichlorobenzene.

13. The method according to claim 1, wherein a) is conducted at a temperature of 60 to 100° C.

14. The method according to claim 1, wherein a) is conducted for a time ranging from 15 minutes to 5 hours.

15. The method according to claim 1, wherein the second solvent is water-whose temperature does not exceed 20° C.

* * * * *